(12) United States Patent
Muquit et al.

(10) Patent No.: US 8,483,449 B2
(45) Date of Patent: Jul. 9, 2013

(54) REGISTRATION DEVICE, CHECKING DEVICE, PROGRAM, AND DATA STRUCTURE

(75) Inventors: Mohammad Abdul Muquit, Kanagawa (JP); Hiroshi Abe, Tokyo (JP)

(73) Assignee: Sony Corporation, Tokyo (JP)

( * ) Notice: Subject to any disclaimer, the term of this patent is extended or adjusted under 35 U.S.C. 154(b) by 787 days.

(21) Appl. No.: 12/600,042

(22) PCT Filed: May 14, 2008

(86) PCT No.: PCT/JP2008/059297
§ 371 (c)(1),
(2), (4) Date: Nov. 13, 2009

(87) PCT Pub. No.: WO2008/143270
PCT Pub. Date: Nov. 27, 2008

(65) Prior Publication Data
US 2010/0208947 A1    Aug. 19, 2010

(30) Foreign Application Priority Data

May 15, 2007    (JP) ................................. 2007-129526

(51) Int. Cl.
*G06K 9/00*    (2006.01)
(52) U.S. Cl.
USPC ......................................... 382/115; 382/128
(58) Field of Classification Search
None
See application file for complete search history.

(56) References Cited

U.S. PATENT DOCUMENTS

| 7,366,331 B2* | 4/2008 | Higuchi | 382/124 |
| 7,634,116 B2* | 12/2009 | Sato | 382/124 |
| 2008/0008365 A1* | 1/2008 | Hikita et al. | 382/124 |
| 2010/0239128 A1* | 9/2010 | Mohammad et al. | 382/115 |

FOREIGN PATENT DOCUMENTS

| EP | 2 146 316 A1 | 1/2010 |
| EP | 2 146 318 A1 | 1/2010 |
| JP | 6-274630 | 9/1994 |
| JP | 06-274630 | 9/1994 |
| JP | 2003-303178 | 10/2003 |
| JP | 2004-054698 | 2/2004 |
| JP | 2004-54698 | 2/2004 |
| JP | 2005-122480 | 5/2005 |
| JP | 2006-330872 | 12/2006 |

OTHER PUBLICATIONS http://math.fullerton.edu/mathews/n2003/leastsquarespoly/LeastSqPolyProof.pdf. Mathews et al; May 2003.*

(Continued)

*Primary Examiner* — Chan S. Park
*Assistant Examiner* — Nancy Bitar
(74) *Attorney, Agent, or Firm* — Finnegan, Henderson, Farabow, Garrett & Dunner, L.L.P.

(57) ABSTRACT

There is proposed a registration apparatus, a verification apparatus, and a program capable of improving authentication accuracy and an identification data structure capable of improving reliability. A blood vessel line included in an image is divided into a plurality of partial lines on the basis of end points and a diverging point of the blood vessel line. Coefficients of terms corresponding to degrees included in a polynomial equation for an n-th order curve representing each of the partial lines are extracted. Data including points at both ends of each of the partial lines and the coefficients is generated.

12 Claims, 10 Drawing Sheets

OTHER PUBLICATIONS

European Search Report from the European Patent Office in corresponding European Application No. 08753025.9, dated Oct. 4, 2012.
Di Ruberto C.; "Recognition of shapes by attributed skeletal graphs", Pattern Recognition, Elsevier, GB, vol. 37, No. 1, Jan. 1, 2004, pp. 21-31.
Luciano Da Fontoura Costa et al., "Shape Concepts" Jan. 1, 2001, Shape Analysis and Classification: Theory and Practice, GB, pp. 265-273.
Anonymous: "Published International Standards Developed by ISO/IEC JTC 1/SC 37—Biometrics". 20070486 Apr. 6, 2007, pp. 1-5.
Johnson R Ed—Bankman I N (Editor): "Arterial Tree Morphometry", Jan. 1, 2000, Handbook of Medical Imaging—Processing and Analysis; [Academic Press Series in Biomedical Engineering,] Academic Press, San Diego, Calif. pp. 261-283.
Jain L C (Ed) et al., "Chapter 2 (part): Fingerprint Feature Processing Techniques and Poroscopy in: Intelligent Biometric Techniques in Fingerprint and Face Recognition", Jan. 1, 1999, pp. 56-60.
ISO/IEC 19794-9:2007—Information Technology—Biometric Data Interchange Formats—Part 9: Vascular Image Data International Standard ISO/IEC Jan. 1, 2007, pp. 1-24.
Luciano Da Fontoura Costa et al: "Shape Analysis and Classifoication: Theory and Practice Passage", Jan. 1, 2001, Shape Analysis and Classification: Theory and Practice, CRC Press, pp. 78-85.

* cited by examiner

(A) BEFORE CONVERSION (B) AFTER CONVERSION

| P4$_1$ | P3$_1$ | P2$_1$ | P1$_1$ | P0$_1$ | xs$_1$ | xe$_1$ |
|---|---|---|---|---|---|---|
| P4$_2$ | P3$_2$ | P2$_2$ | P1$_2$ | P0$_2$ | xs$_2$ | xe$_2$ |
| P4$_3$ | P3$_3$ | P2$_3$ | P1$_3$ | P0$_3$ | xs$_3$ | xe$_3$ |
| ⋮ | ⋮ | ⋮ | ⋮ | ⋮ | ⋮ | ⋮ |
| P4$_N$ | P3$_N$ | P2$_N$ | P1$_N$ | P0$_N$ | xs$_N$ | xe$_N$ |

ORIGINAL BLOOD　　RESTORED BLOOD
   VESSEL LINE　　　　VESSEL LINE

REGISTRATION DEVICE, CHECKING DEVICE, PROGRAM, AND DATA STRUCTURE

CROSS REFERENCE TO RELATED APPLICATIONS

This application is a national phase application based on PCT/JP2008/059297, filed May 14, 2008, which claims the priority of Japanese Patent Application No. 2007-129526, filed May 15, 2007, the contents of all of which are incorporated herein by reference.

TECHNICAL FIELD

The present invention relates to a registration apparatus, a verification apparatus, a program, and a data structure, and is preferably applied to biometrics authentication.

BACKGROUND ART

In resent years, blood vessels have been employed as one of the subjects of biometric authentication. As a related art of such biometric authentication, an authentication apparatus has been proposed for extracting end points and a diverging point of a blood vessel on a captured image as feature points and generating data to be registered or data to be compared with registered data from the extracted feature points (see, for example, Patent Document 1). As compared with an authentication apparatus for setting image data itself as data to be registered, this authentication apparatus can markedly reduce memory occupancy of data to be stored.

Patent Document 1: Japanese Unexamined Patent Application Publication No. 2003-303178

However, since the end points and the diverging point are separate from one another on a blood vessel, they are unreliable data for making a determination whether a person is a registrant. Accordingly, even if feature points generated as data to be compared with registered data are the same as feature points generated as the registered data, the probability of determining that a person who is not a registrant is the registrant or a person who is the registrant is not the registrant by mistake due to external factors such as an image capturing environment and noise or internal factors such as (the difference between individuals in) the difficulty in capturing the image of blood vessels of living organisms is high. That is, the accuracy of authentication (the accuracy of determination whether a person is a registrant) is low.

DISCLOSURE OF INVENTION

The present invention has been made in view of the above-described background, and proposes a registration apparatus, a verification apparatus, and a program capable of improving authentication accuracy and a data structure capable of improving reliability.

In order to solve the above-described difficulties, the present invention provides a registration apparatus including: dividing means for dividing a blood vessel line included in an image into a plurality of partial lines on the basis of end points and a diverging point of the blood vessel line; extracting means for extracting coefficients of terms corresponding to degrees included in a polynomial equation for an n-th order curve representing each of the plurality of partial lines; and generating means for generating data including points at both ends of each of the plurality of partial lines and the coefficients.

Furthermore, the present invention provides a verification apparatus including: storing means for storing data including points at both ends of each of a plurality of partial lines into which a blood vessel line included in an image is divided on the basis of end points and an diverging point of the blood vessel line and including coefficients of terms corresponding to degrees included in a polynomial equation for an n-th order curve representing each of the plurality of partial lines; restoring means for restoring the blood vessel line using the points at both ends of each of the plurality of partial lines and the coefficients; and verifying means for comparing the blood vessel line restored by the restoring means with a blood vessel line set as a subject to be compared with the blood vessel line.

Still furthermore, the present invention provides a program for causing, using a work memory, an image processing unit for performing predetermined processing upon an image to execute: dividing a blood vessel line included in an image into a plurality of partial lines on the basis of end points and a diverging point of the blood vessel line; extracting coefficients of terms corresponding to degrees included in a polynomial equation for an n-th order curve representing each of the plurality of partial lines; and generating data including points at both ends of each of the plurality of partial lines and the coefficients.

Still furthermore, the present invention provides a data structure of identification data generated as data to be registered. The identification data has a structure including points at both ends of each of a plurality of partial lines into which a blood vessel line included in an image is divided on the basis of end points and a diverging point of the blood vessel line and including coefficients of terms corresponding to degrees included in a polynomial equation for an n-th order curve representing each of the plurality of partial lines. The identification data is used for processing for determining whether a person is a registrant on the basis of a degree of similarity.

As described previously, according to the present invention, since not only feature points of a blood vessel line but also coefficients of terms corresponding to degrees included in a polynomial equation for an n-th order curve representing each of a plurality of partial lines are extracted as data representing the shape of the blood vessel line, it is possible to discretely represent the blood vessel line using curves that are close to the blood vessel line. As a result, it is possible to reduce the effect of external factors such as an image capturing environment and noise or internal factors such as (the difference between individuals in) the difficulty in capturing the image of blood vessels of living organisms. Thus, there can be provided a registration apparatus, a verification apparatus, and a program capable of improving authentication accuracy and an identification data structure capable of improving reliability.

BEST MODES FOR CARRYING OUT THE INVENTION

An embodiment of the present invention will be described in detail below with reference to the accompanying drawings.

(1) Entire Configuration of Authentication Apparatus

Figure 1:
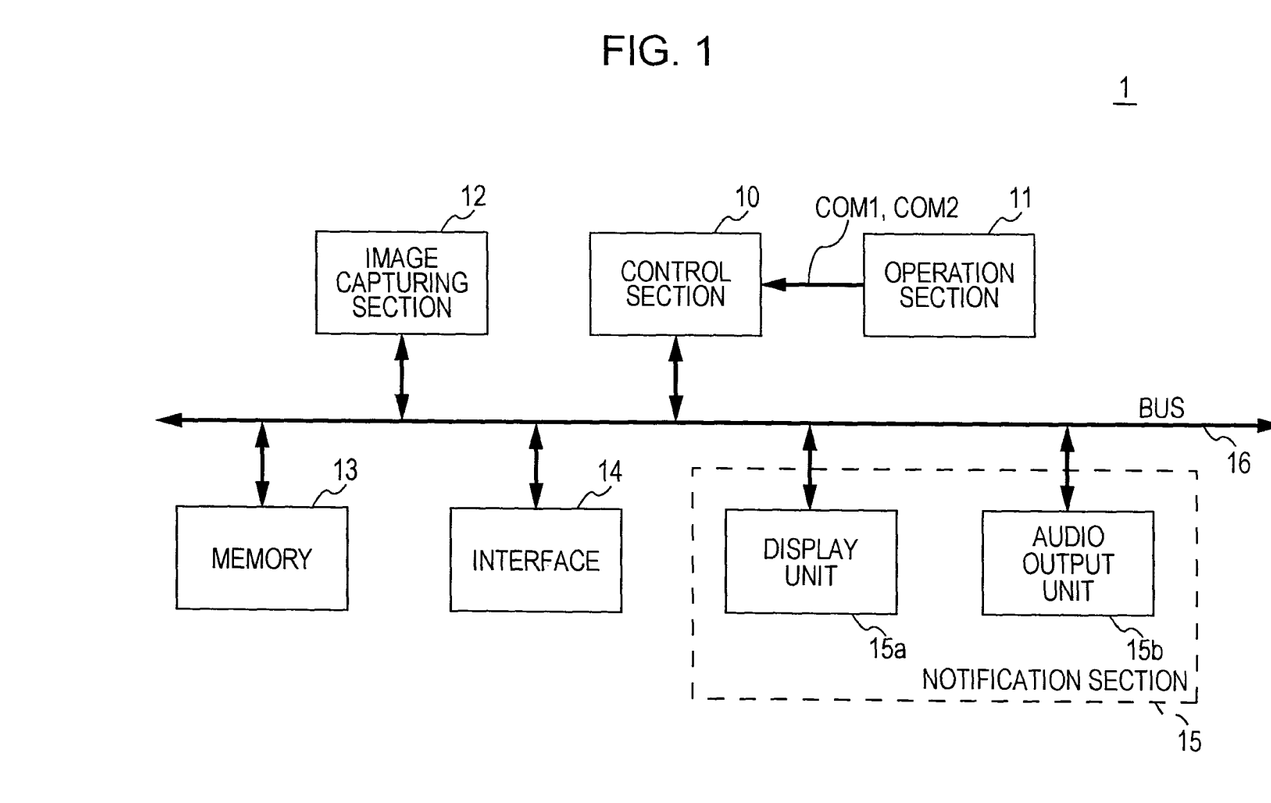
FIG. 1 is a block diagram illustrating an entire configuration of an authentication apparatus according to an embodiment of the present invention.

FIG. 1 illustrates the entire configuration of an authentication apparatus 1 according to an embodiment of the present invention. The authentication apparatus 1 is configured by connecting an operation section 11, an image capturing section 12, a memory 13, an interface 14, and a notification section 15 to a control section 10 via a bus 16.

The control section 10 is a computer that includes a Central Processing Unit (CPU) for performing overall control of the authentication apparatus 1, a Read-Only Memory (ROM) for storing various programs and setup information, a Random Access Memory (RAM) functioning as a work memory for the CPU, and an image processing unit.

An execution command COM1 for executing a mode (hereinafter referred to as a blood vessel registration mode) of registering blood vessels of a user to be registered (hereinafter referred to as a registrant) or an execution command COM 2 for executing a mode (hereinafter referred to as an authentication mode) of determining whether the registrant is present is input from the operation section 11 into the control section 10 in accordance with a user operation.

The control section 10 determines a mode to be executed on the basis of the execution command COM1 or the execution command COM2, and executes the blood vessel registration mode or the authentication mode by appropriately controlling the image capturing section 12, the memory 13, the interface 14, and the notification section 15 in accordance with a program corresponding to a result of the mode determination.

The image capturing section 12 has a camera that sets space over a finger placement area on the housing of the authentication apparatus 1 as image capturing space, and adjusts the lens position of an optical system of the camera, the diaphragm value of a diaphragm of the camera, and the shutter speed (exposure time) of an image pickup element of the camera in accordance with a setting value set by the control section 10.

Furthermore, the image capturing section 12 has a near infrared light source for emitting near infrared light to the image capturing space. The image capturing section 12 turns on the near infrared light source for a time period specified by the control section 10, periodically captures an image of a subject which is reflected on an image capturing surface of the image pickup element, and sequentially outputs pieces of image data of images generated from the image capturing to the control section 10.

The memory 13 is, for example, a flash memory. The memory 13 stores data in an area specified by the control section 10 or reads out data stored in the area.

The interface 14 transmits and receives various pieces of data to and from an external apparatus connected thereto via a predetermined transmission path.

The notification section 15 includes a display unit 15a and an audio output unit 15b. The display unit 15a displays characters and figures on a display screen on the basis of display data transmitted from the control section 10. On the other hand, the audio output unit 15b outputs sound from a speaker on the basis of audio data transmitted from the control section 10.

(1-1) Blood Vessel Registration Mode

Next, the blood vessel registration mode will be described. If the blood vessel registration mode is determined as a mode to be executed, the control section 10 sets the operation mode to the blood vessel registration mode and causes the notification section 15 to make a notification that a finger has to be placed in the image capturing space.

At that time, the control section 10 causes the camera included in the image capturing section 12 to perform an image capturing operation, and turns on the near infrared light source included in the image capturing section 12.

In this state, if a finger is placed in the image capturing space, near infrared light outputs from the near infrared light source, passes through the inside of the finger, and enters the image pickup element through the optical system and diaphragm of the camera as light that projects a blood vessel. As a result, an image of the blood vessel in the finger is projected on the image capturing surface of the image pickup element. Accordingly, the image of the blood vessel is included in an image based on image data generated as a result of the image capturing performed by the image capturing section 12.

Figure 2:
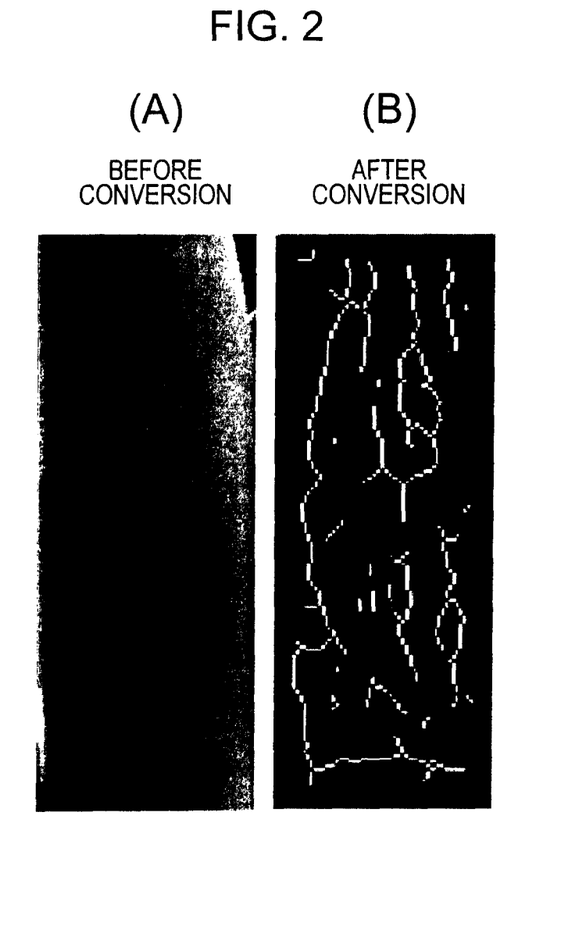
FIG. 2 are schematic diagrams illustrating an image obtained before pattern conversion and an image obtained after pattern conversion.

The control section 10 performs pieces of preprocessing such as image rotation compensation, noise removal, and image clipping upon image data transmitted from the image capturing section 12 as appropriate, and generates a binary image (FIG. 2(B)) in which blood vessels are expressed as a pattern from a multilevel image (FIG. 2(A)) obtained after the preprocessing as illustrated in, for example, FIG. 2.

To take an example of a concrete method of generating the binary image, the control section 10 highlights the outlines of blood vessels included in a target image obtained after the preprocessing using a Gaussian filter and a differential filter such as a Log filter and converts the target image with the highlighted outlines into a binary image on the basis of a set brightness value. Subsequently, the control section 10 extracts from the binary image centers of the widths of the blood vessels or brightness peaks of the widths of the blood vessels so as to obtain a pattern of lines with the same width representing the blood vessels. In this embodiment, the blood vessels are represented as a pattern of lines with the same width of one pixel. Such blood vessels having the same line width are hereinafter referred to as blood vessel lines.

Furthermore, if the control section 10 generates a binary image, it extracts a parameter representing the shape of blood vessel lines included in the binary image (hereinafter referred to as a shape parameter), generates data to be identified including the shape parameter (hereinafter referred to as identification data), and registers the identification data by storing the identification data in the memory 13.

Thus, the control section 10 can execute the blood vessel registration mode.

(1-2) Authentication Mode

Next, the authentication mode will be described. If the authentication mode is determined as a mode to be executed, the control section 10 sets the operation mode to the authentication mode, causes the notification section 15 to make a notification that a finger has to be placed in the image capturing space, causes the camera included in the image capturing section 12 to perform an image capturing operation, and turns on the near infrared light source. Subsequently, the control section 10 performs pieces of preprocessing such as image rotation compensation, noise removal, and image clipping upon image data transmitted from the image capturing section 12 as appropriate.

Furthermore, the control section 10 generates a binary image from an image obtained as a result of the preprocessing like in the blood vessel registration mode, and restores blood vessel lines from the shape parameter that is stored in the memory 13 as the identification data.

Subsequently, the control section 10 compares blood vessel lines included in the generated binary image with the restored blood vessel lines (performs pattern matching). As a result of the comparison, a similarity level (the degree of correlation) among these blood vessel lines is obtained. The control section 10 determines whether a person can be approved as a registrant in accordance with the similarity level.

If it is determined that the person cannot be approved as the registrant, the control section 10 visually and aurally notifies the person of the fact through the display unit 15a and the audio output unit 15b. On the other hand, if it is determined that the person can be approved as the registrant, the control section 10 transmits data indicating that the person has been approved as the registrant to an apparatus connected to the interface 14. In response to the data indicating that the person has been approved as the registrant, the apparatus connected to the interface 14 performs predetermined processing that should be performed when the authentication is successfully performed, for example, locking a door for a predetermined time period or releasing a restricted operation mode.

Thus, the control section 10 can execute the authentication mode.

(2) Details of Feature Point Extraction Process Performed by Control Section

Next, the feature point extraction process performed by the control section 10 will be described in detail.

(2-1) Detection of End Point and Diverging Point

Figure 3:
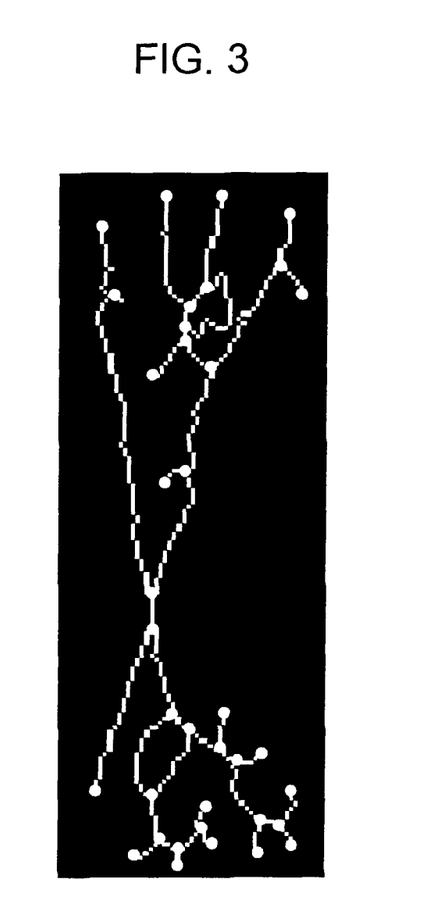
FIG. 3 is a schematic diagram illustrating an image from which end points and diverging points are detected.

If the control section 10 generates a binary image, it detects end points and diverging points from points (pixels) of a blood vessel line included in the binary image as illustrated in, for example, FIG. 3.

(2-2) Extraction of Blood Vessel Line Shape Parameter

Subsequently, the control section 10 divides the blood vessel line into partial lines (hereinafter referred to as partial blood vessel lines) on the basis of the end points and the diverging points, expresses each of the partial blood vessel lines in the form of a polynomial equation for an n-th order curve, extracts the coefficients of terms corresponding to degrees included the polynomial equation for an n-th order curve (hereinafter referred to as polynomial coefficients), and sets the polynomial coefficients of each of the partial blood vessel lines and points at both ends of each of the partial blood vessel lines as a blood vessel line shape parameter.

Figure 4:
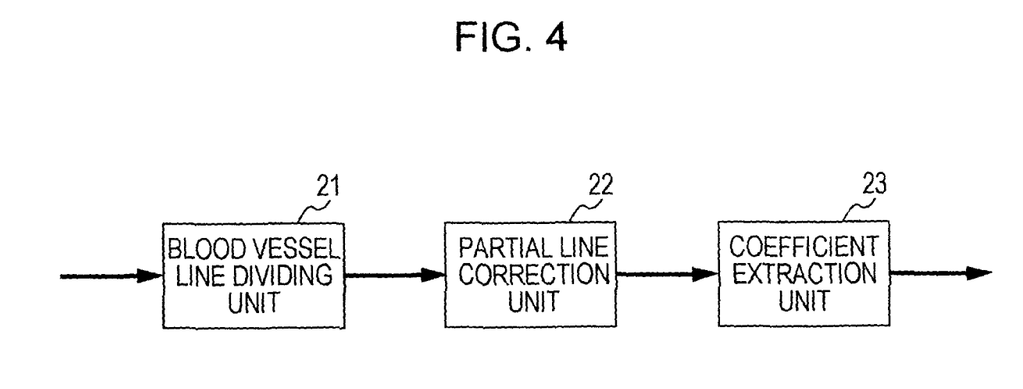
FIG. 4 is a block diagram illustrating a functional configuration of a control section for performing processing for extracting a control point.

An exemplary method of extracting the shape parameter will be described. As illustrated in FIG. 4, the control section 10 functions as a blood vessel line dividing unit 21, a partial line correction unit 22, and a coefficient extraction unit 23 in performing this extraction method. The details of processing operations performed by the blood vessel line dividing unit 21, the partial line correction unit 22, the coefficient extraction unit 23, and a coefficient extraction unit 24 will be described below.

(2-2-1) Division of Blood Vessel Line

The blood vessel line dividing unit 21 divides a blood vessel line into partial blood vessel lines each of which extends from an end point or a diverging point to the next end point or the next diverging point.

Figure 5:
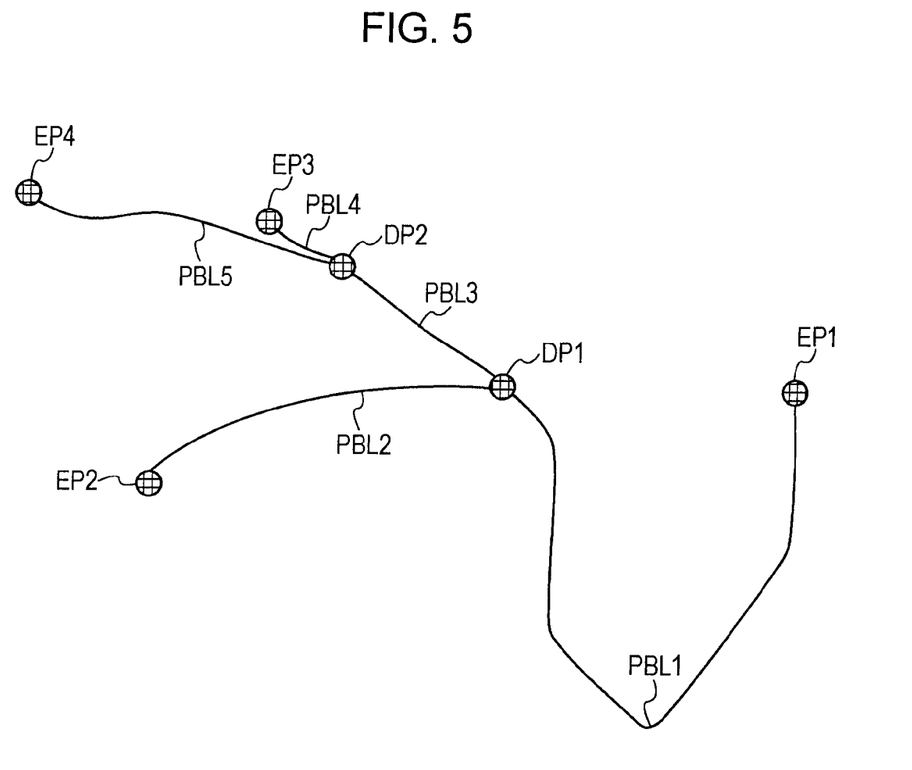
FIG. 5 is a schematic diagram illustrating an example of a blood vessel line that is divided on the basis of end points and diverging points.

For example, in a case illustrated in FIG. 5, the blood vessel line dividing unit 21 divides a blood vessel line into a partial blood vessel line PBL1 extending from a diverging point DP1 set as a starting point to another feature point (an end point EP1) that appears after the diverging point DP1 and is set as a terminal point, a partial blood vessel line PBL2 extending from the diverging point DP1 set as the starting point to another feature point (an end point EP2) that appears after the diverging point DP1 and is set as a terminal point, and a partial blood vessel line PBL3 extending from the diverging point DP1 set as the starting point to another feature point (a diverging point DP2) that appears after the diverging point DP1 and is set as a terminal point. The blood vessel line dividing unit 21 similarly divides the blood vessel line into a partial blood vessel line PBL4 extending from the diverging point DP2 set as a starting point to another feature point (an end point EP3) that appears after the diverging point DP2 and is set as a terminal point and a partial blood vessel line PBL5 extending from the diverging point DP2 set as the starting point to another feature point (an end point EP4) that appears after the diverging point DP2 and is set as a terminal point.

In the case illustrated in FIG. 5, although only the diverging points DP1 and DP2 are set as the starting points, an end point and a diverging point may be set as the starting points. As is apparent from FIG. 5, an end point can only be either a starting point or a terminal point, while a diverging point can be either or both of a starting point and a terminal point.

(2-2-2) Correction of Partial Blood Vessel Line

Next, the partial line correction unit 22 detects the length (the number of pixels) of each of the partial blood vessel lines and the types of points at both ends of each of the partial blood vessel lines, and deletes a partial blood vessel line in accordance with a result of the detection.

That is, if the partial line correction unit 22 detects a partial blood vessel line having a length (the number of pixels) shorter than a predetermined threshold length from the partial blood vessel lines into which the blood vessel line has been divided, it determines whether one of points at both ends of the partial blood vessel line is an end point.

At that time, if one of points at both ends of the partial blood vessel line is an end point, this means that the partial blood vessel line is located at the end of the blood vessel line. In this case, the partial line correction unit 22 determines that the effect of the partial blood vessel line on the entire blood vessel line is very small and the feature part of the partial blood vessel line is unreliable, and deletes the partial blood vessel line without removing a diverging point included in the partial blood vessel line. In the case illustrated in FIG. 5, the partial line correction unit 22 deletes, for example, the partial blood vessel line PBL4 without removing the diverging point DP2.

On the other hand, if one of points at both ends of the partial blood vessel line is not an end point, this means that the points at both ends of the partial blood vessel line are diverging points and the partial blood vessel line is located in the middle of the blood vessel line.

Figure 6:
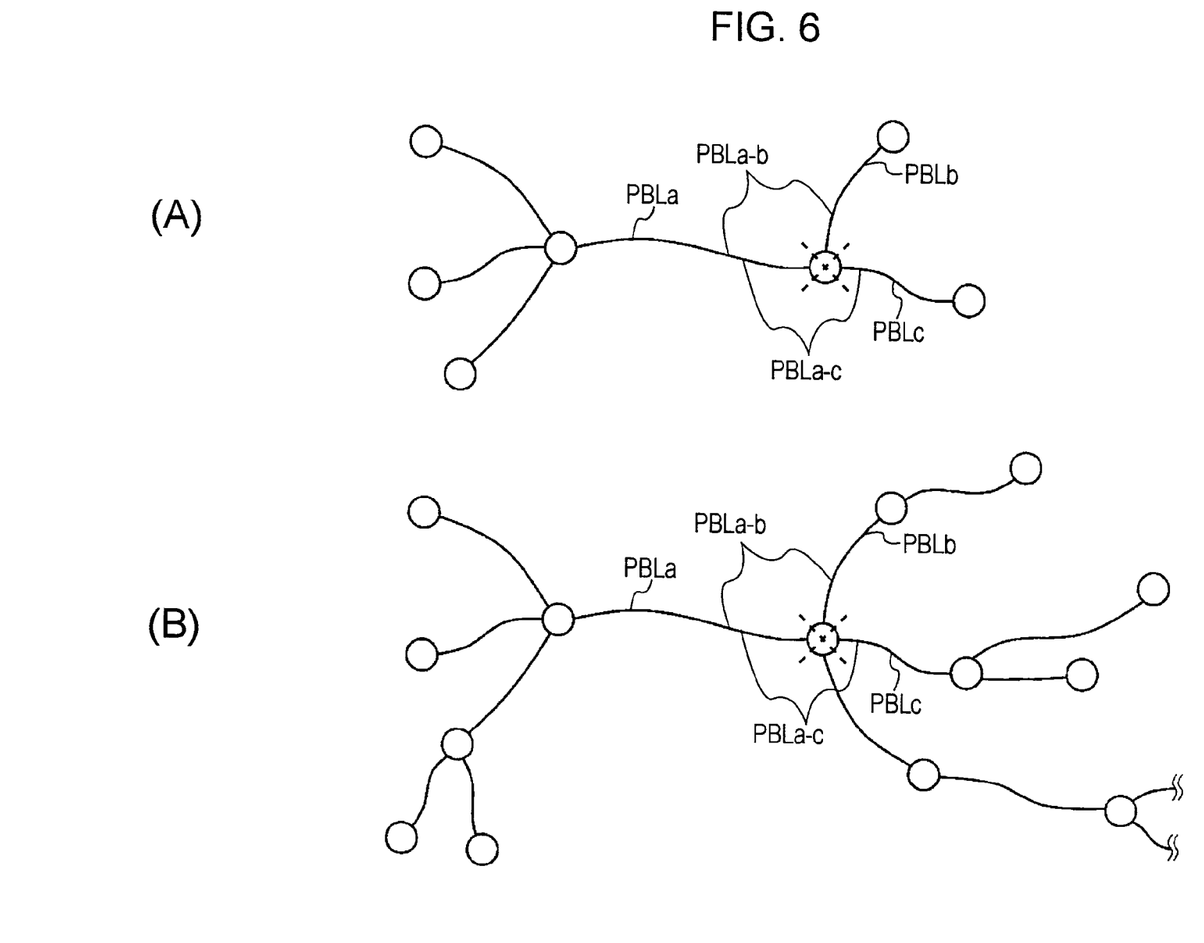
FIG. 6 are schematic diagrams used to describe the connection of partial blood vessel lines.

In this case, the partial line correction unit 22 compares the number of partial blood vessel lines connected to one of the diverging points of the partial blood vessel line with that connected to the other one of the diverging points of the partial blood vessel line. As illustrated in, for example, FIG. 6(A), if the number of partial blood vessel lines connected to one of diverging points of a partial blood vessel line differs from that connected to the other one of the diverging points of the partial blood vessel line, the partial line correction unit 22 deletes the partial blood vessel line by deleting one of the diverging points of the partial blood vessel line which is connected to a smaller number of partial blood vessel lines and connecting the partial blood vessel line to adjacent partial blood vessel lines.

In a case illustrated in FIG. 6(A), the partial line correction unit 22 forms a partial blood vessel line PBLa-b by connecting a partial blood vessel line PBLa to a partial blood vessel line PBLb and forms a partial blood vessel line PBLa-c by connecting the partial blood vessel line PBLa to a partial blood vessel line PBLc, thereby deleting the partial blood vessel line PBLa.

Figure 9:
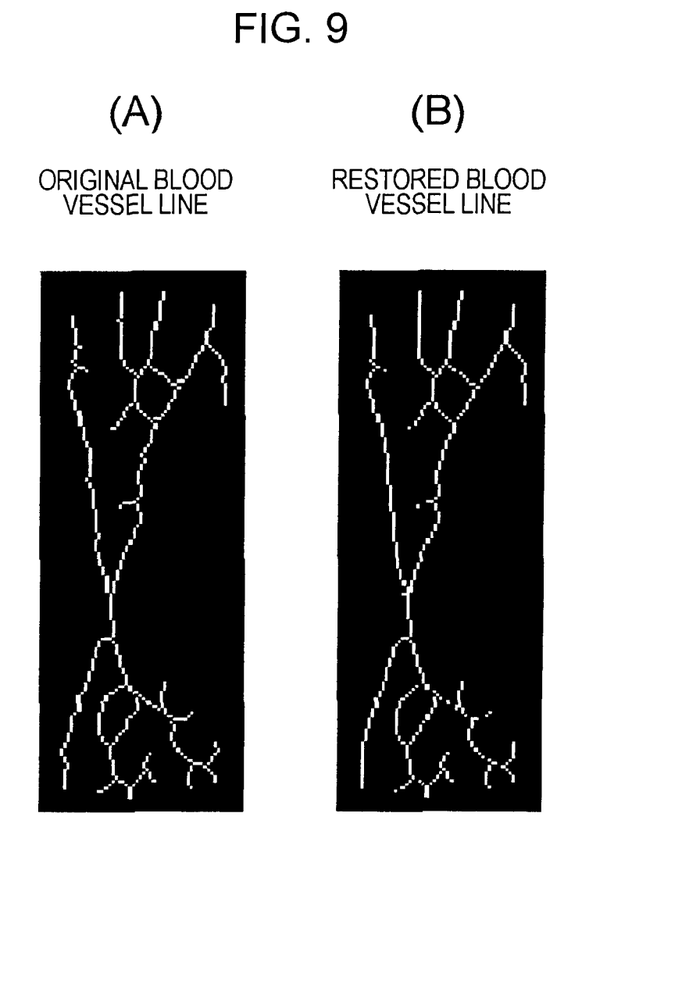
FIG. 9 are schematic diagrams illustrating an original blood vessel line and a restored blood vessel line.

On the contrary, as illustrated in, for example, FIG. 9(B), if the number of partial blood vessel lines connected to one of the diverging points of the partial blood vessel line is the same as that connected to the other one of the diverging points of the partial blood vessel line, the partial line correction unit 22 compares the number of end points included in partial blood vessel lines connected to one of the diverging points of the partial blood vessel line with that included in partial blood vessel lines connected to the other one of the diverging points of the partial blood vessel line, and deletes the partial blood vessel line by deleting one of the diverging points of the partial blood vessel line which is connected to the partial blood vessel lines including a smaller number of end points and connecting the partial blood vessel line to adjacent partial blood vessel lines.

In a case illustrated in FIG. 6(B), like in the case illustrated in FIG. 6(A), the partial line correction unit 22 forms the partial blood vessel line PBLa-b by connecting the partial blood vessel line PBLa to the partial blood vessel line PBLb and forms the partial blood vessel line PBLa-c by connecting the partial blood vessel line PBLa to the partial blood vessel line PBLc, thereby deleting the partial blood vessel line PBLa.

Thus, the partial line correction unit 22 deletes a partial blood vessel line having a length shorter than a predetermined length, thereby preventing the extraction of polynomial coefficients for a featureless partial blood vessel line and reducing the number of polynomial coefficients.

(2-2-3) Extraction of Polynomial Coefficient

Subsequently, the coefficient extraction unit 23 extracts polynomial coefficients for each of the partial blood vessel lines (coefficients obtained when each of the partial blood vessel lines is represented by a polynomial equation for an n-th order curve).

More specifically, if the coefficient extraction unit 23 selects a partial blood vessel line to be processed from among the partial blood vessel lines, it substitutes each of points (hereinafter referred to as blood vessel forming points) included in the selected partial blood vessel line into the following polynomial equation for an n-th order curve.

$$y = p_1 x^n + p_2 x^{n-1} + \ldots + p_n x + p_{n+1} \quad (1)$$

For example, if the number of blood vessel forming points is m, m polynomial equations are obtained as follows. Here, $p_1, p_2, \ldots,$ and $p_{(n+1)}$ included in equations (1) and (2) represent coefficients of terms corresponding to degrees, that is, polynomial coefficients.

$$y_1 = p_1 x_1^n + p_2 x_1^{n-1} + \ldots + p_n x_1 + p_{n+1}$$

$$y_2 = p_1 x_2^n + p_2 x_2^{n-1} + \ldots + p_n x_2 + p_{n+1}$$

$$y_m = p_1 x_m^n + p_2 x_m^{n-1} + \ldots + p_n x_m + p_{n+1} \quad (2)$$

Subsequently, if the coefficient extraction unit 23 makes the substitutions of the blood vessel forming points into equation (1), it changes polynomial coefficients $p_1, p_2, \ldots,$ and $p_{(n+1)}$ included in a plurality of polynomial equations obtained from these substitutions until the differences in value between the left sides and the right sides of these polynomial equations become the minimum and extracts the polynomial coefficients $p_1, p_2, \ldots,$ and $p_{(n+1)}$.

Thus, the coefficient extraction unit 23 can extract the polynomial coefficients $p_1, p_2, \ldots,$ and $p_{(n+1)}$ obtained when a curve is closest to the blood vessel forming points included in the partial blood vessel line.

Figure 7:
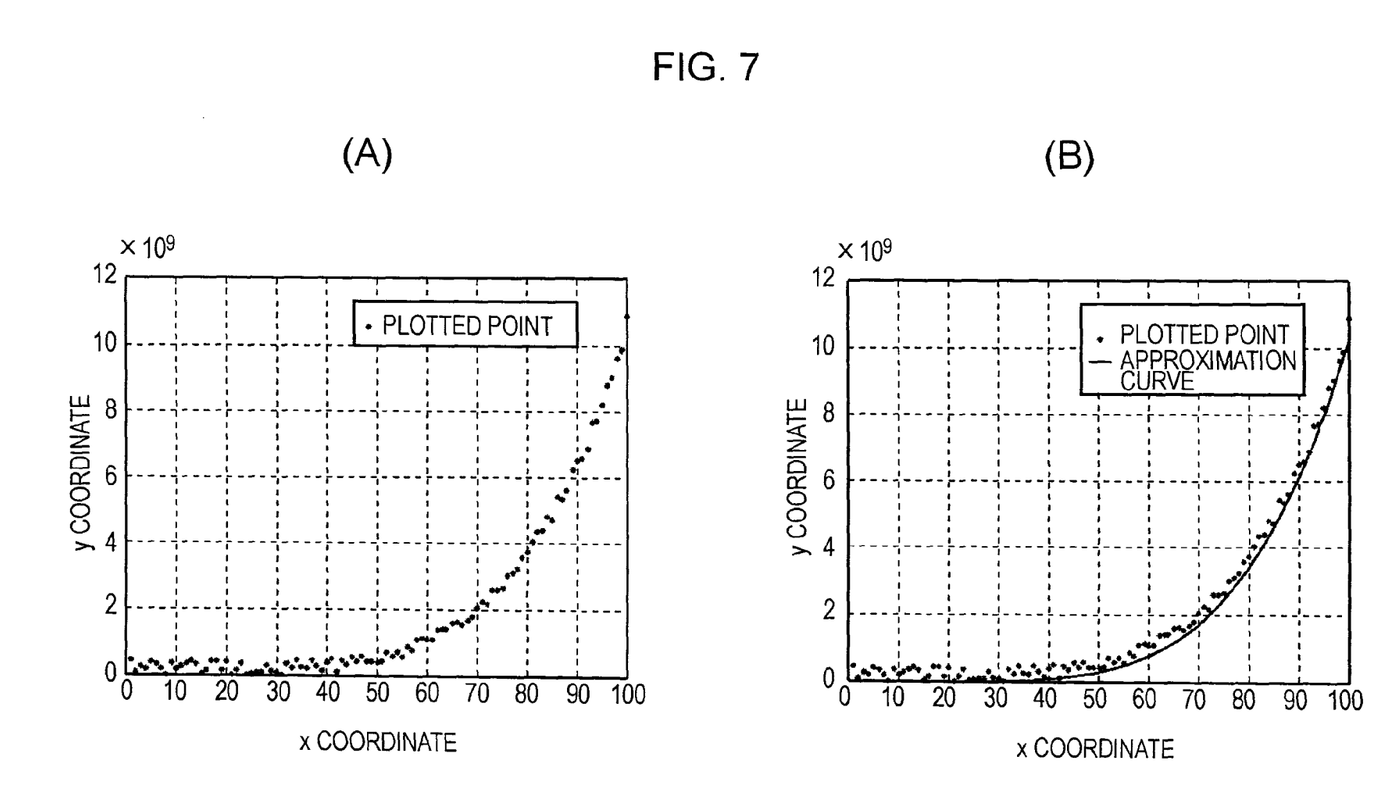
FIG. 7 are schematic diagrams illustrating a plurality of given points and a fifth order curve that is closest to these points.

Here, FIG. 7 illustrates a plurality of given points and a fifth order curve that is closest to these points. As is apparent from FIG. 7, polynomial coefficients extracted by the coefficient extraction unit 23 are polynomial coefficients obtained when a curve is closest to an actual partial blood vessel line. Accordingly, the extracted polynomial coefficients serve as reliable elements when the partial blood vessel line is restored.

(2-3) Generation of Identification Data

After completing the above-described extraction process, the control section 10 functions as an identification data generation unit for generating identification data that includes polynomial coefficients for each of the partial blood vessel lines, the positions of points at both ends of each of the partial blood vessel lines, and an identifier indicating that the polynomial coefficients have been obtained as a result of the above-described extraction process (hereinafter referred to as a content certification identifier), and registers the generated identification data in the memory 13 (FIG. 1).

Figure 8:
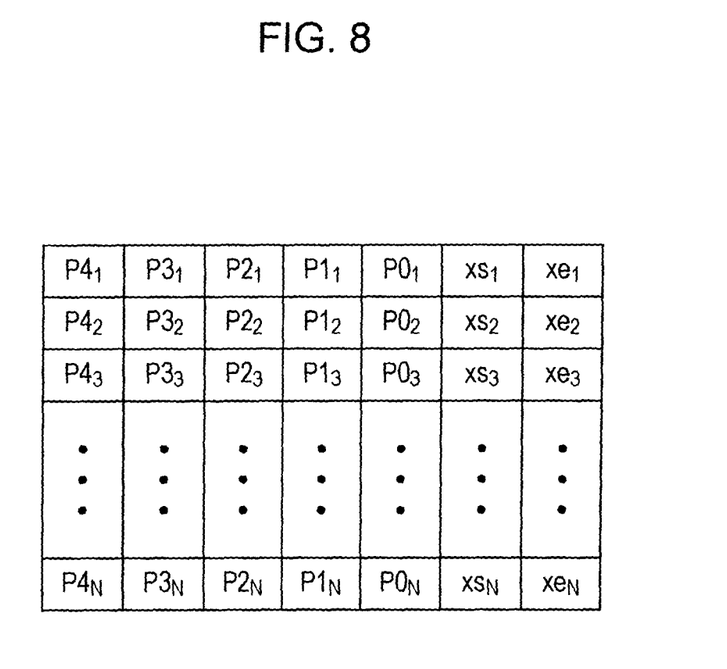
FIG. 8 is a schematic diagram illustrating an example of a data structure of identification data.

FIG. 8 illustrates an exemplary data structure of the identification data. The identification data includes a header region HAr and a data region DAr. The header region HAr stores the content certification identifier, for example, a version related to the extraction process.

On the other hand, if the number of partial blood vessel lines is represented by i (i=2, 3, 4, ..., N (N is integer)), a fourth order coefficient, a third order coefficient, a second order coefficient, a first order coefficient, and a zeroth order coefficient that are polynomial coefficients included in a polynomial equation for a fourth order curve are represented by P4, P3, P2, P1, and P0, respectively, and the x coordinates of points at both ends of each of the partial blood vessel lines (that is, the range of each of the partial blood vessel lines in the x direction) are represented by xs and xe, the data region DAr stores polynomial coefficients P4i to P0i of each of partial blood vessel lines 1 to N and positions xsi and xei of points at both ends of each of the partial blood vessel lines 1 to N in the form of, for example, a matrix.

If each of the partial blood vessel lines 1 to N is restored using data stored in the data region DAr, the values of the polynomial coefficients P4i to P0i are substituted into equation (1) and then the values of x coordinates of points from the point xsi to the point xei are input into equation (1). As a result, it is possible to obtain the values of y coordinates of the points from the point xsi to the point xei and generate curves that are close to the partial blood vessel lines 1 to N.

FIG. 9 illustrates a result of comparison between an original blood vessel line and a blood vessel line that is restored by using in equation (1) the polynomial coefficients P4i to P0i for each of the partial blood vessel lines which have been extracted in the above-described extraction process.

As is apparent from a result of the comparison, the identification data indicates using the content certification identifier stored in the header region HAr that the polynomial coefficients P4i to P0i, which are stored in the data region DAr for each of the partial blood vessel lines 1 to N, are elements having a high degree of reproducibility of an actual blood vessel line. As a result, a data structure capable of certifying that the polynomial coefficients P4i to P0i are highly reliable can be obtained.

(3) Details of Authentication Process Performed by Control Section

Figure 10:
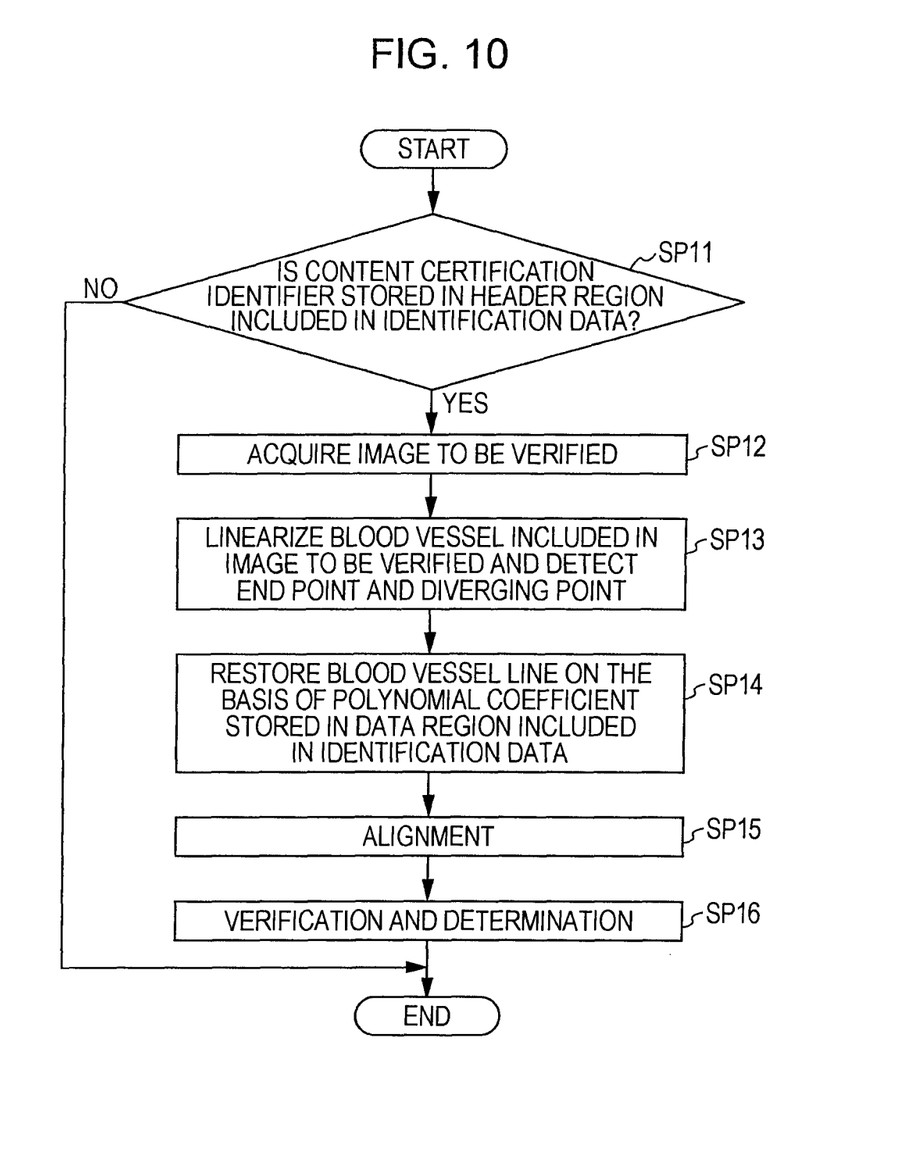
FIG. 10 is a flowchart illustrating an authentication process.

Next, the authentication process performed by the control section 10 in the authentication mode will be described in detail with reference to a flowchart illustrated in FIG. 10.

If the control section 10 receives the execution command COM2 from the operation section 11 (FIG. 1), it starts the authentication process. In step SP11, the control section 10 reads out identification data stored in the memory 13 and determines whether a content certification identifier is stored in the header region HAr (FIG. 8) of the identification data.

If the content certification identifier is not stored, this means that data stored in the data region DAr (FIG. 8) is data of an unreliable subject to be subjected to biometric identification. In this case, the control section 10 deletes the identification data read out from the memory 13 and terminates the authentication process.

On the other hand, if the content certification identifier is stored, in step SP12, the control section 10 controls the image capturing section 12 (FIG. 1) so as to acquire image data to be verified. In step SP13, the control section 10 performs predetermined preprocessing upon the image data as appropriate and detects end points and diverging points included in a blood vessel line on an image that is obtained as a result of the preprocessing.

In step SP14, the control section 10 generates curves corresponding to the partial blood vessel lines 1 to N on the basis of the polynomial coefficients P4 to P0 stored in the data region DAr (FIG. 8) included in the identification data read out from the memory 13 in step SP11, thereby restoring a blood vessel line.

In step SP15, the control section 10 calculates the amount of correction (the amount of movement) by rotating and moving in parallel, on the basis of end points and diverging points included in the restored blood vessel line, the diverging points and the end points that have been detected in step SP13 from the blood vessel line on the image to be verified, and performs an alignment between the restored blood vessel line and the blood vessel line included in the image to be verified on the basis of the amount of correction (the amount of movement). In step SP16, the control section 10 determines whether a registrant is present by comparing these aligned blood vessel lines with each other.

For example, if it is clear from a result of the comparison that the percentage of the number of overlapping pixels of the aligned blood vessel lines is equal to or larger than a predetermined threshold value, the control section 10 determines that a person can be approved as the registrant. On the contrary, if the percentage is smaller than the threshold value, the control section 10 determines that the person cannot be approved as the registrant.

Thus, if the content certification identifier is not stored in the header region HAr (FIG. 8) of the identification data, the control section 10 determines that data included in the data region DAr (FIG. 8) of the identification data is data of an unreliable subject to be subjected to biometric identification and terminates the process of restoring a blood vessel line on the basis of the data stored in the data region DAr. As a result, it is possible to prevent the comparison between a blood vessel line to be verified and a blood vessel line that is restored on the basis of stored data other than stored data that has been extracted with given extraction accuracy and to prevent the decrease in authentication accuracy.

(4) Operation and Effect

As described previously, the control section 10 divides a blood vessel line into a plurality of partial blood vessel lines on the basis of the end points and diverging points of the blood vessel line, expresses each of the partial blood vessel lines in the form of a polynomial equation for an n-th order curve, and extracts the coefficients (polynomial coefficients) of terms corresponding to degrees included in the polynomial equation.

Subsequently, the control section 10 generates identification data (FIG. 8) including the polynomial coefficients of each of the partial blood vessel lines and the positions (values of x coordinates) of points at both ends of each of the partial blood vessel lines.

Accordingly, the control section 10 can express not only the connection relationship between the partial blood vessel lines but also the shapes of the partial blood vessel lines using the polynomial coefficients of each of the partial blood vessel lines and the positions (values of x coordinates) of the points at both ends of each of the partial blood vessel lines, that is, can discretely express the blood vessel line using curves that are close to the blood vessel line.

As a result, the probability of determining that a person who is not a registrant is the registrant or a person who is the registrant is not the registrant by mistake due to external factors such as an image capturing environment and noise or internal factors such as (the difference between individuals in) the difficulty in capturing the image of blood vessels of living organisms can be reduced. Furthermore, memory occupancy of data to be registered can be reduced.

It is possible to perform this coefficient extraction process with an addition less than that required in an exemplary case in which a partial blood vessel line is made to be close to a Bezier curve and the control point sequences of the partial blood vessel line that is close to the Bezier curve are extracted. The amount of memory required in this embodiment for storage of the values of coefficients corresponding to degrees and the values of x coordinates is smaller than that required in a case in which control point sequences are employed, because the case requires the amount of memory for storage of the values of x coordinates and y coordinates of the control point sequences corresponding to degrees. Accordingly, from the viewpoint of a processing addition and the amount of information, this embodiment is preferable to a case in which a general known curve function is used.

In this embodiment, the control section 10 generates the identification data (FIG. 8) including not only polynomial coefficients of each of partial blood vessel lines and the positions (values of x coordinates) of points at both ends of each of the partial blood vessel lines but also an identifier (content certification identifier) indicating that these polynomial coefficients have been extracted through a predetermined extraction process.

In this extraction process, the substitutions of points included in each of the partial blood vessel lines into a polynomial equation for an n-th order curve are performed, and coefficients of terms corresponding to degrees included in a plurality of polynomial equations obtained from these substitutions are changed until the differences in value between the left sides and the right sides of these polynomial equations become the minimum and are then extracted.

Accordingly, since the control section 10 can represent that the extracted coefficients are polynomial coefficients extracted when a curve that is closest to blood vessel forming points included in each of actual partial blood vessel lines is obtained, it can certify that the identification data itself is highly reliable and prevent the probability of determining that a person who is not a registrant is the registrant or a person who is the registrant is not the registrant by mistake.

According to the above-described configuration, by extracting coefficients (polynomial coefficients) of terms corresponding to degrees included in a polynomial equation for an n-th order curve representing each of a plurality of partial blood vessel lines and generating identification data including the coefficients for each of the partial blood vessel lines and the positions of points at both ends of each of the partial blood vessel lines, it is possible to restore not only the connection relationship between these partial blood vessel lines but also the shapes of these partial blood vessel lines. Accordingly, the authentication apparatus 1 capable of reducing the effect of external factors such as an image capturing environment and noise or internal factors such as (the difference between individuals in) the difficulty in capturing the image of blood vessels of living organisms and improving authentication accuracy can be obtained.

(5) Other Embodiments

In the above-described embodiment, the case in which x-direction coefficients are extracted using equation (1) as coefficients of terms corresponding to degrees included in a polynomial equation for an n-th order curve representing a partial blood vessel line has been described. However, the present invention is not limited to the case, and y-direction coefficients may be obtained using the following equation. However, since blood vessel lines have the property of extending in substantially the same direction, it is desirable that coefficients for a direction that is the same as a blood vessel line extending direction be obtained.

$$x = p_1 y^n + p_2 y^{n-1} + \ldots + p_n y + p_{n+1} \quad (3)$$

Furthermore, in the above-described embodiment, the case in which coefficients of terms corresponding to degrees included in a polynomial equation for an n-th order curve representing a partial blood vessel line are fixed, that is, the order of a curve is fixed has been described. However, the present invention is not limited to the case, and the order of a curve may be changed in accordance with the degree of roughness of a curve representing the partial blood vessel line.

More specifically, for example, if the number of points at which a line connecting points at both ends of a partial blood vessel line to each other and the partial blood vessel line cross each other is larger, coefficients of terms corresponding to degrees included in a polynomial equation for a higher n-th order curve representing the partial blood vessel line are extracted. As a result, it is possible to more accurately extract coefficients representing the shape of the blood vessel line. This leads to the improvement of authentication accuracy.

Furthermore, in the above-described embodiment, the case in which blood vessel lines included in an image are made to have the same width has been described. However, these blood vessel lines do not necessarily have the same width. Even if these blood vessel lines do not have the same width, effects similar to those obtained in the above-described embodiment can be obtained.

Still furthermore, in the above-described embodiment, the case in which the above-described shape parameter extraction process is performed in accordance with a program stored in a ROM has been described. However, the present invention is not limited to the case. The above-described shape parameter extraction process may be performed in accordance with a program that has been installed from a program storage medium such as a Compact Disc (CD), a Digital Versatile Disc (DVD), or a semiconductor memory or has been downloaded from a program providing server on the Internet.

Still furthermore, in the above-described embodiment, the case in which a program and the image processing unit cooperate with each other in performing the above-described shape parameter extraction process has been described. However, a part of the above-described shape parameter extraction process may be performed by an independent piece of hardware.

Still furthermore, in the above-described embodiment, the case in which the authentication apparatus 1 having an image capturing function, a verification function, and a registration function is used has been described. However, the present invention is not limited to the case, and apparatuses that individually have these functions or parts of these functions may be used in accordance with an application purpose.

INDUSTRIAL APPLICABILITY

The present invention is applicable to a biometrics authentication field.

EXPLANATION OF REFERENCE

1: AUTHENTICATION APPARATUS, 10: CONTROL SECTION, 11: OPERATION SECTION, 12: IMAGE CAPTURING SECTION, 13: MEMORY, 14: INTERFACE, 15: NOTIFICATION SECTION, 15a: DISPLAY UNIT, 15b: AUDIO OUTPUT UNIT, 21: BLOOD VESSEL LINE DIVIDING UNIT, 22: PARTIAL LINE CORRECTION UNIT, 23: COEFFICIENT EXTRACTION UNIT

The invention claimed is:

1. A registration apparatus characterized by comprising:
dividing means for dividing a blood vessel line included in an image into a plurality of partial lines on the basis of end points and a diverging point of the blood vessel line;
extracting means for extracting coefficients of terms corresponding to degrees included in a polynomial equation for an n-th order curve representing each of the plurality of partial lines, characterized in that the extracting means performs substitutions of points included in each of the plurality of partial lines into the polynomial equation for an n-th order curve, changes coefficients of terms corresponding to degrees included in a plurality of polynomial equations obtained from the substitutions until differences in value between left sides and right sides of the plurality of polynomial equations become the minimum, and extracts the coefficients; and
generating means for generating data including points at both ends of each of the plurality of partial lines and the coefficients.

2. The registration apparatus according to claim 1, characterized in that,
   the registration apparatus further includes deleting means for deleting a partial line having a length shorter than a predetermined length from the plurality of partial lines, and
   the extracting means extracts coefficients of terms corresponding to degrees included in a polynomial equation for an n-th order curve representing each of remaining ones of the plurality of partial lines which have not deleted by the deleting means.

3. The registration apparatus according to claim 1, characterized in that the extracting means changes an order of the n-th order curve in accordance with a degree of roughness of the blood vessel line.

4. The registration apparatus according to claim 1, characterized in that, when the number of points at which a line connecting points at both ends of each of the plurality of partial lines with each other and the partial line cross each other is larger, the extracting means extracts coefficients of terms corresponding to degrees included in a polynomial equation for a higher n-th order curve representing the partial line.

5. The registration apparatus according to claim 1, characterized in that the generating means generates data including the points at both ends of each of the plurality of partial lines, the coefficients, and an identifier indicating that the coefficients have been extracted through a predetermined extraction process.

6. The registration apparatus according to claim 5, characterized in that,
   the extracting means performs substitutions of points included in each of the plurality of partial lines into the polynomial equation for an n-th order curve, changes coefficients of terms corresponding to degrees included in a plurality of polynomial equations obtained from the substitutions until differences in value between left sides and right sides of the plurality of polynomial equations become the minimum, and extracts the coefficients, and
   the generating means generates data including the identifier indicating that the coefficients have been extracted through the predetermined extraction process performed by the extracting means.

7. A verification apparatus characterized by comprising:
   storing means for storing data including points at both ends of each of a plurality of partial lines into which a blood vessel line included in an image is divided on the basis of end points and an diverging point of the blood vessel line and including coefficients of terms corresponding to degrees included in a polynomial equation for an n-th order curve representing each of the plurality of partial lines, characterized in that the coefficients have been extracted through a predetermined extraction process, and
   in the predetermined extraction process, substitutions of points included in each of the plurality of partial lines into the polynomial equation for an n-th order curve are performed, and coefficients of terms corresponding to degrees included in a plurality of polynomial equations obtained from the substitutions are changed until differences in value between left sides and right sides of the plurality of polynomial equations become the minimum and are then extracted;
   restoring means for restoring the blood vessel line using the points at both ends of each of the plurality of partial lines and the coefficients; and
   verifying means for comparing the blood vessel line restored by the restoring means with a blood vessel line set as a subject to be compared with the blood vessel line.

8. The verification apparatus according to claim 7, characterized in that, when the data does not include an identifier indicating that the coefficients have been extracted through a predetermined extraction process, the restoring means stops restoring of the blood vessel line.

9. A non-transitory computer-readable storage medium encoded with a computer program for causing an image processing unit to perform predetermined processing upon an image to execute:
   dividing a blood vessel line included in an image into a plurality of partial lines on the basis of end points and a diverging point of the blood vessel line;
   extracting coefficients of terms corresponding to degrees included in a polynomial equation for an n-th order curve representing each of the plurality of partial lines, characterized in that the extracting means performs substitutions of points included in each of the plurality of partial lines into the polynomial equation for an n-th order curve, changes coefficients of terms corresponding to degrees included in a plurality of polynomial equations obtained from the substitutions until differences in value between left sides and right sides of the plurality of polynomial equations become the minimum, and extracts the coefficients; and
   generating data including points at both ends of each of the plurality of partial lines and the coefficients.

10. A non-transitory computer-readable storage medium encoded with a data structure of identification data generated as data to be registered characterized in that,
    the identification data has a structure including points at both ends of each of a plurality of partial lines into which a blood vessel line included in an image is divided on the basis of end points and a diverging point of the blood vessel line and including coefficients of terms corresponding to degrees included in a polynomial equation for an n-th order curve representing each of the plurality of partial lines, characterized in that the coefficients have been extracted through a predetermined extraction process, and
    the predetermined extraction process is a process of performing substitutions of points included in each of the plurality of partial lines into the polynomial equation for an n-th order curve, changing coefficients of terms corresponding to degrees included in a plurality of polynomial equations obtained from the substitutions until differences in value between left sides and right side of the plurality of polynomial equations become the minimum, and extracting the coefficients, and
    the identification data is used for processing for determining whether a person is a registrant on the basis of a degree of similarity.

11. The data structure according to claim 10, characterized in that,
    the points at both ends of each of the plurality of partial lines and the coefficients are used for processing for restoring the blood vessel line, and
    the restored blood vessel line is used for processing for determining whether a person is a registrant on the basis of a degree of similarity between a restored blood vessel line and a blood vessel line set as a subject to be compared with the restored blood vessel line.

12. The data structure according to claim 10, characterized in that, the identification data has a structure including the points at both ends of each of the plurality of partial lines, the coefficients, and an identifier indicating that the coefficients have been extracted through a predetermined extraction process.

* * * * *